(12) United States Patent
Bamford et al.

(10) Patent No.: US 7,297,693 B2
(45) Date of Patent: Nov. 20, 2007

(54) NITROGEN-CONTAINING HETEROCYCLIC COMPOUNDS AND THEIR USE AS RAF INHIBITORS

(75) Inventors: Mark James Bamford, Harlow (GB); David Kenneth Dean, Harlow (GB); Antoinette Naylor, Harlow (GB); Andrew Kenneth Takle, Harlow (GB); David Matthew Wilson, Harlow (GB)

(73) Assignee: SmithKline Beecham P.L.C., Middlesex (GB)

( * ) Notice: Subject to any disclaimer, the term of this patent is extended or adjusted under 35 U.S.C. 154(b) by 483 days.

(21) Appl. No.: 10/488,579

(22) PCT Filed: Sep. 5, 2002

(86) PCT No.: PCT/EP02/09942

§ 371 (c)(1),
(2), (4) Date: Mar. 4, 2004

(87) PCT Pub. No.: WO03/022836

PCT Pub. Date: Mar. 20, 2003

(65) Prior Publication Data

US 2004/0209883 A1    Oct. 21, 2004

(30) Foreign Application Priority Data

Sep. 5, 2001    (GB) ................... 0121494.9

(51) Int. Cl.
*A61K 31/506* (2006.01)
*A61K 31/443* (2006.01)
*A61K 31/4439* (2006.01)
*C07D 401/04* (2006.01)
*C07D 405/04* (2006.01)
*C07D 405/14* (2006.01)
*C07D 407/14* (2006.01)

(52) U.S. Cl. ............................... 514/235.5; 514/253.1; 514/299; 514/304; 514/316; 514/318; 514/336; 514/343; 344/121; 344/131; 546/112; 546/125; 546/187; 546/193; 546/279.1; 546/284.7

(58) Field of Classification Search ............... 544/121, 544/131; 546/112, 125, 187, 193, 279.1, 546/284.7; 514/235.5, 253.1, 299, 304, 316, 514/318, 336, 343
See application file for complete search history.

(56) References Cited

FOREIGN PATENT DOCUMENTS

| WO | WO 00/25791 | 5/2000 |
|---|---|---|
| WO | WO 01/66540 | 9/2001 |

OTHER PUBLICATIONS

Wermuth, C.G. (ed.), "Chapter 13: Molecular Variations Based on Isosteric Replacements", *The Practice of Medicinal Chemistry*, pp. 204-237, Academic Press Ltd., Copyright (1996), XP-002190259.

*Primary Examiner*—Bernard Dentz
(74) *Attorney, Agent, or Firm*—Grace C. Hsu; Mary E. McCarthy; Charles M. Kinzig

(57) ABSTRACT

Compounds and their use as pharmaceuticals particularly as Raf kinase inhibitors for the treatment of neurotraumatic diseases, cancer, chronic neurodegeneration, pain, migraine and cardiac hypertrophy.

8 Claims, No Drawings

NITROGEN-CONTAINING HETEROCYCLIC COMPOUNDS AND THEIR USE AS RAF INHIBITORS

This application is a §371 national stage filing of PCT/EP02/09942 filed 5 Sep. 2002.

This invention relates to novel compounds and their use as pharmaceuticals, particularly as Raf kinase inhibitors for the treatment of neurotraumatic diseases, cancer chronic neurodegeneration, pain, migraine and cardiac hypertrophy.

Raf protein kinases are key components of signal transduction pathways by which specific extracellular stimuli elicit precise cellular responses in mammalian cells. Activated cell surface receptors activate ras/rap proteins at the inner aspect of the plasma-membrane which in turn recruit and activate Raf proteins. Activated Raf proteins phosphorylate and activate the intracellular protein kinases MEK1 and MEK2. In turn, activated MEKs catalyse phosphorylation and activation of p42/p44 mitogen-activated protein kinase (MAPK). A variety of cytoplasmic and nuclear substrates of activated MAPK are known which directly or indirectly contribute to the cellular response to environmental change. Three distinct genes have been identified in mammals that encode Raf proteins; A-Raf, B-Raf and C-Raf (also known as Raf-1) and isoformic variants that result from differential splicing of mRNA are known.

Inhibitors of Raf kinases have been suggested for use in disruption of tumor cell growth and hence in the treatment of cancers, e.g. histiocytic lymphoma, lung adenocarcinoma, small cell lung cancer and pancreatic and breast carcinoma; also in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery and/or during childbirth; also in chronic neurodegeneration such as Alzheimer's disease and Parkinson's disease; also in the treatment of pain, migraine and cardiac hypertrophy.

We have now found a group of novel compounds that are inhibitors of Raf kinases, in particular inhibitors of B-Raf kinase.

According to the invention there is provided compounds of formula (I):

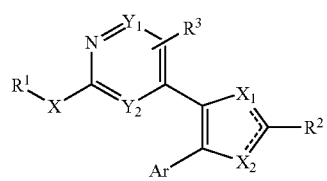

(I)

wherein;

X is O, $CH_2$, CO, S or NH, or the moiety X—$R^1$ is hydrogen;

$Y_1$ and $Y_2$ independently represent CH or N;

$R^1$ is hydrogen, $C_{1-6}$alkyl, $C_{3-7}$cycloalkyl, aryl, aryl$C_{1-6}$alkyl-, heterocyclyl, heterocyclyl$C_{1-6}$alkyl-, heteroaryl, or heteroaryl$C_{1-6}$alkyl-, any of which, except hydrogen, may be optionally substituted;

$R^2$ is $CONR^6R^7$;

$R^6$ and $R^7$ independently represent hydrogen, $C_{1-6}$alkyl, $C_{3-7}$cycloalkyl, aryl, aryl$C_{1-6}$alkyl, heteroaryl, heteroaryl$C_{1-6}$alkyl, heterocyclyl, or heterocyclyl$C_{1-6}$alkyl, any of which except for hydrogen may be optionally substituted, or $R^6$ and $R^7$ together with the nitrogen atom to which they are attached form a 3- to 12-membered monocyclic or bicyclic ring optionally including upto three heteroatoms selected from O, N or S wherein said ring may be optionally substituted;

Ar is a group of the formula a) or b):

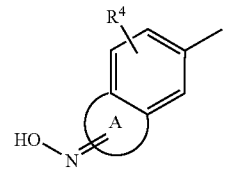

a)

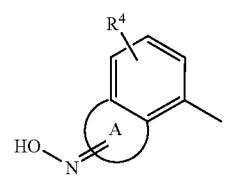

b)

wherein A represents a fused 5- to 7-membered ring optionally containing up to two heteroatoms selected from O, S and $NR^5$, wherein $R^5$ is hydrogen or $C_{1-6}$alkyl, which ring is optionally substituted by up to 2 substituents selected from halogen, $C_{1-6}$alkyl, hydroxy, $C_{1-6}$alkoxy or keto;

$R^3$ and $R^4$ are independently selected from hydrogen, halogen, $C_{1-6}$alkyl, aryl, aryl$C_{1-6}$alkyl, $C_{1-6}$alkoxy, $C_{1-6}$alkoxy$C_{1-6}$alkyl, halo$C_{1-6}$alkyl, aryl$C_{1-6}$alkoxy, hydroxy, nitro, cyano, azido, amino, mono- and di-N-$C_{1-6}$alkylamino, acylamino, arylcarbonylamino, acyloxy, carboxy, carboxy salts, carboxy esters, carbamoyl, mono- and di-N-$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkyl sulphinyl or $C_{1-6}$alkylsulphonyl; and one of $X_1$ and $X_2$ is selected from O, S or $NR^{11}$ and the other is CH, wherein $R^{11}$ is hydrogen, $C_{1-6}$alkyl, aryl or aryl$C_{1-6}$alkyl;

or pharmaceutically acceptable salts thereof.

As used herein, the double bond indicated by the dotted lines of formula (I), represents the possible regioisomeric ring forms of the compounds falling within the scope of this invention, the double bond being between the non-heteroatoms.

The hydroxyimino moiety can be positioned on any of carbon atoms of the non-aromatic ring in groups a) and b).

The hydroxyimino moiety can exist as either the E or Z isomer or as a mixture of both. Alkyl and alkenyl groups referred to herein, individually or as part of larger groups e.g. alkoxy, may be straight or branched groups containing up to six carbon atoms and are optionally substituted by one or more groups selected from the group consisting of aryl, heteroaryl, heterocyclyl, $C_{1-6}$alkoxy, $C_{1-6}$alkylthio, aryl$C_{1-6}$alkoxy, aryl$C_{1-6}$alkylthio, amino, mono- or di-$C_{1-6}$alkylamino, cycloalkyl, cycloalkenyl, carboxy and esters thereof, amide, sulphonamido, ureido, guanidino, $C_{1-6}$alkylguanidino, amidino, $C_{1-6}$alkylamidino, $C_{1-6}$acyloxy, azido, hydroxy, hydroxyimino and halogen.

Cycloalkyl and cycloalkenyl groups referred to herein include groups having from three to seven ring carbon atoms and are optionally substituted as described hereinabove for alkyl and alkenyl groups.

Optional substituents for alkyl, alkenyl, cycloalkyl and cycloalkenyl groups include aryl, heteroaryl, heterocyclyl, $C_{1-6}$alkoxy, $C_{1-6}$alkylthio, aryl$C_{1-6}$alkoxy, aryl$C_{1-6}$alkylthio, amino, mono- or di-$C_{1-6}$alkylamino, aminosulphonyl, cycloalkyl, cycloalkenyl, carboxy and esters thereof, amide, ureido, quanidino, $C_{1-6}$alkylquanidino, amidino, $C_{1-6}$alkylamidino, $C_{1-6}$acyloxy, hydroxy, and halogen or any combination thereof. Preferably the substituents are mono-or di-$C_{1-6}$alkylamino, heterocyclo$C_{1-6}$alkylamino or $C_{2-6}$acylamino.

Alternatively the optional substituent contains a water-solubilising group; suitable solubilising moieties will be apparent to those skilled in the art and include hydroxy and amine groups. Even more preferably the optional substituent includes amino, mono- or di-$C_{1-6}$alkylamino, amine containing heterocyclyl, or hydroxy or any combination thereof.

When used herein, the term "aryl" includes, unless otherwise defined, single and fused rings suitably containing from 4 to 7, preferably 5 or 6, ring atoms in each ring, which rings, may each be unsubstituted or substituted by, for example, up to three substituents.

Suitable aryl groups include phenyl and naphthyl, such as 1-naphthyl or 2-naphthyl.

When used herein in respect of $R^6$ or $R^7$, the term "monocyclic ring" means a 3 to 7 membered ring system for example phenyl, pyrrole, pyrroline, pyrrolidine, piperidine, morpholine, thiomorpholine, piperizine, indole or indoline. The term "bicyclic ring" means a 7 to 12 membered fused ring system e.g napthyl.

When used herein hetero$C_{1-6}$alkyl- means a $C_{1-6}$ carbon chain wherein the end carbon atom in the chain is substituted by a heteroatom selected from N, O, or S for example $C_{1-6}$alkylamino, $C_{1-6}$alkyloxy or $C_{1-6}$alkylthio.

$C_{1-6}$alkylhetero$C_{1-6}$alkyl means a $C_{3-13}$alkyl chain wherein one of the carbon atoms has been replaced with a heteroatom selected from N, O, or S, for example $C_{1-6}$alkylamino$C_{1-6}$alkyl or $C_{1-6}$ alkylaminodi$C_{1-6}$alkyl, $C_{1-6}$alkyloxy$C_{1-6}$alkyl-, $C_{1-6}$alkylthio$C_{1-6}$alkyl-, or $C_{1-6}$alkylthiodi$C_{1-6}$alkyl.

When used herein the term "heterocyclyl" includes, unless otherwise defined, non-aromatic, single or fused, saturated or unsaturated, rings suitably containing up to four heteroatoms in each ring, each of which is selected from O, N and S, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring. Examples of heterocyclyl groups include pyrrolidine, piperidine, piperazine, morpholine, thiomorpholine, imidazolidine and pyrazolidine.

When used herein, the term "heteroaryl" includes, unless otherwise defined, mono- and bicyclic heteroaromatic ring systems comprising up to four, preferably 1 or 2, heteroatoms each selected from O, N and S. Each ring may have from 4 to 7, preferably 5 or 6, ring atoms. A bicyclic heteroaromatic ring system may include a carbocyclic ring. Examples of heteroaryl groups include pyrrole, quinoline, isoquinoline, pyridine, pyrimidine, oxazole, thiazole, thiadiazole, triazole, imidazole and benzimidazole.

When used herein (except for in respect of $R^6$ and $R^7$), the term "mono-cyclic" means an aromatic or heteroaromatic group having a 3 to 8 membered ring system for example phenyl, pyridine or pyran. When used herein the term "bicyclic ring" means an aromatic or heteroaromatic fused ring system in which at least one of the rings is aromatic or heteroaromatic for example naphthyl, indole, benzofuran, indene, fused phenylcyclohexane, or fused phenyl cyclopentane.

Aryl, heterocyclyl, heteroaryl groups and mono and bicyclic ring systems may be optionally substituted by preferably up to three substituents. Suitable substituents include halogen, hydroxy, $C_{1-6}$alkyl, aryl, aryl$C_{1-6}$alkyl, $C_{1-6}$alkoxy, $C_{1-6}$alkoxy$C_{1-6}$alkyl, halo$C_{1-6}$alkyl, aryl$C_{1-6}$alkoxy, hydroxy, nitro, cyano, azido, amino, mono- and di-N-$C_{1-6}$alkylamino, acylamino, arylcarbonylamino, acyloxy, carboxy, carboxy salts, carboxy esters, carbamoyl, mono- and di-N-$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkylsulphinyl, $C_{1-6}$alkylsulphonyl, heterocyclyl, heteroaryl, heterocyclyl $C_{1-6}$alkyl, hydroxyimino-$C_{1-6}$alkyl and heteroaryl $C_{1-6}$alkyl, and combinations thereof.

Preferably the optional substituent contains a water-solubilising group; suitable solubilising moieties will be apparent to those skilled in the art and include hydroxy and amine groups. Even more preferably the optional substituent includes amino, mono- or di-$C_{1-6}$alkylamino, amine containing heterocycle or hydroxy or any combination thereof. Other preferred substituents are $C_{1-6}$alkyl and $C_{1-6}$alkoxy$C_{1-6}$alkyl.

When used herein the term halo represents fluoro, chloro, bromo or iodo.

X is preferably NH or X—$R^1$ is preferably hydrogen.

When X is NH, $R^1$ is preferably hydrogen or $C_{1-6}$alkyl.

When $Y_1$ and $Y_2$ are CH, X—$R^1$ is preferably hydrogen.

When $Y_2$ is N, $R^1$ is preferably hydrogen or $C_{1-6}$alkyl.

Preferably $R^{11}$ is hydrogen.

Most preferably X—$R^1$ is hydrogen

Preferably $X^1$ or $X_2$ is S or O, most preferably O.

A is preferably a fused 5 membered ring optionally containing up to two heteroatoms selected from O, S and $NR^5$, wherein $R^5$ is hydrogen or $C_{1-6}$alkyl, which ring is optionally substituted by up to 2 substituents selected from halogen, $C_{1-6}$alkyl, hydroxy, $C_{1-6}$alkoxy or keto.

Even more preferably A is a fused 5 membered ring.

Preferably $R^6$ and $R^7$ are independently selected from hydrogen, $C_{1-6}$alkyl, aryl, heterocyclic and heterocyclic$C_{1-6}$alkyl wherein any of the groups except hydrogen may be optionally substituted or $R^6$ and $R^7$ together with the nitrogen atom to which they are attached form a 3- to 7-membered monocyclic optionally including upto three heteroatoms selected from O, N or S wherein said ring may be optionally substituted.

Most preferably the compounds of the invention are of formula (II);

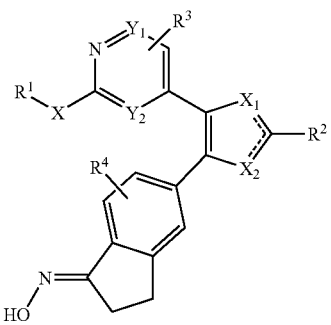

(II)

wherein $R^1$, X, $Y_1$, $Y_2$, $R^3$, $X_1$, $X_2$, $R^2$ and $R^4$ are as defined for compounds of formula (I) or pharmaceutically acceptable salts thereof.

The compounds of formula (I) preferably have a molecular weight of less than 800.

Preferred substituents for the group Ar include halo, hydroxy, hydroxy$C_{1-6}$alkyl, hydroxyimino-$C_{1-6}$alkyl and $C_{1-6}$alkoxy.

It will be understood that the invention includes pharmaceutically acceptable derivatives of compounds of formula (I) and that these are included within the scope of the invention.

Particular compounds according to the invention include those mentioned in the examples and their pharmaceutically acceptable salts. As used herein "pharmaceutically acceptable derivatives" includes any pharmaceutically acceptable salt, ester or salt of such ester of a compound of formula (I) which, upon administration to the recipient, is capable of providing (directly or indirectly) a compound of formula (I) or an active metabolite or residue thereof.

It will be appreciated that for use in medicine the salts of the compounds of formula (I) should be pharmaceutically acceptable. Suitable pharmaceutically acceptable salts will be apparent to those skilled in the art and include those described in *J. Pharm. Sci.*, 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amounts of water.

The invention extends to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Compounds of formula (I) are furan, pyrrole and thiophene derivatives which may be readily prepared, using procedures well-known to those skilled in the art, from starting materials which are either commercially available or can be prepared from such by analogy with well-known processes. For instance see, W. Friedrichsen (p351, furans), R. J. Sundberg (p119, pyrroles) and J. Nakayama (p607, thiophenes) in *Comprehensive Heterocyclic Chemistry II*, volume 2, series eds. A. R. Katritzky, C. W. Rees and E. F. V. Scriven.

Typically, compounds of this invention may be prepared by a sequential transition metal catalysed cross-coupling procedure on a 2,3-dihalo heterocycle, as shown in Scheme 1; this is particularly applicable for furan or thiophene derivatives, i.e. when either $X_1$ or $X_2$ are O or S. For example, Suzuki coupling of pyridine-4-boronic acid with 2,3-dibromofuran-5-carboxylic acid t-butyl ester (1) preferentially results in the formation of the 2-(4-pyridyl) derivative (2). Subsequent Suzuki reaction with an indanone boronic acid derivative (3, wherein PG is O, N—OMe or another ketone protecting group) then generates the derivative (4). Thereafter, the ester group may be converted into an amide group using appropriate conventional functional group interconversion procedures and the group PG converted into an hydroxyimino group as in (5). It will also be appreciated, to one skilled in the art, that the above cross-coupling reactions may be carried out in reverse order giving access to the regioisomeric heterocycles (6).

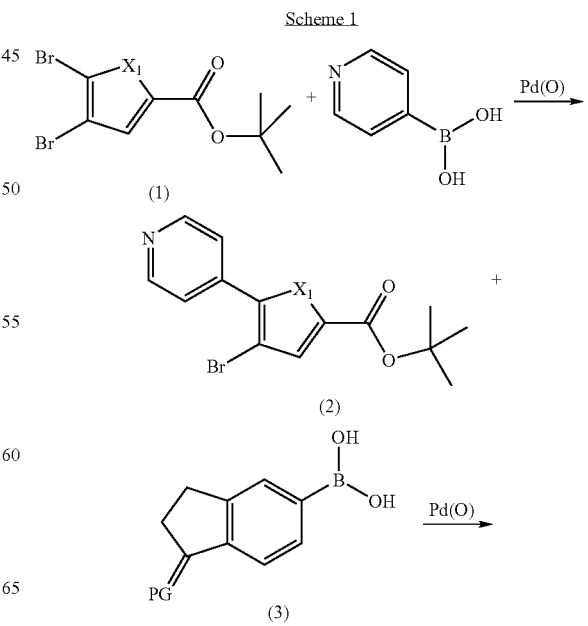

Scheme 1

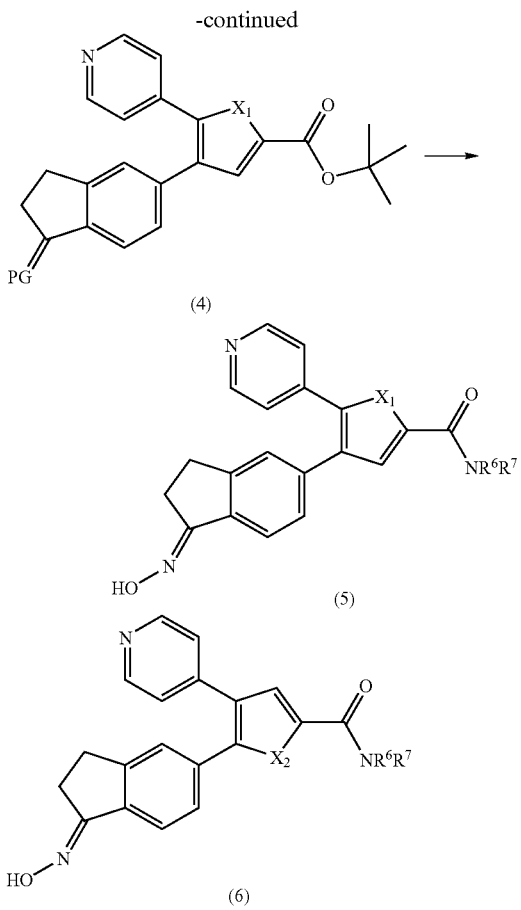

wherein $X_1$, $X_2$, $R^6$ and $R^7$ are as defined for compounds of formula (I), and PG is a protecting group.

During the synthesis of the compounds of formula (I) labile functional groups in the intermediate compounds, e.g. hydroxy, carboxy and amino groups, may be protected. A comprehensive discussion of the ways in which various labile functional groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991).

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof.

Pharmaceutically acceptable salts may be prepared conventionally by reaction with the appropriate acid or acid derivative.

The novel carboxylic esters and the corresponding acids of formula (III) which are used as intermediates in the synthesis of the compounds of formula (I) and (II) also form part of the present invention:

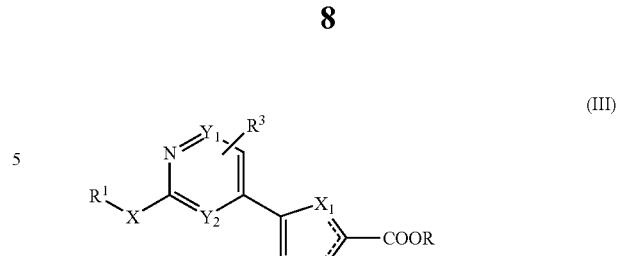

wherein X, $Y_1$, $Y_2$, $R^1$, $R^3$, Ar, $X_1$ and $X_2$ are as defined for compounds of formula (I) and R is hydrogen, $C_{1-6}$alkyl or aryl$C_{1-6}$alkyl.

As indicated above the compounds of formula (I) and their pharmaceutically acceptable derivatives are useful for the treatment and/or prophylaxis of disorders in which Raf kinases, in particular B-Raf kinase, are implicated.

According to a further aspect of the invention there is provided the use of a compound of formula (I) or a pharmaceutically acceptable salt thereof as an inhibitor of B-Raf kinase.

As indicated above the compounds of formula (I) and their pharmaceutically acceptable derivatives are useful in the treatment and/or prophylaxis of disorders associated with neuronal degeneration resulting from ischemic events, cancer, as well as chronic neurodegeneration, pain, migraine and cardiac hypertropy.

According to a further aspect of the invention there is provided a method of treatment or prophylaxis of a neurotraumatic disease, in a mammal in need thereof, which comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of any disease state in a human, or other mammal, which is exacerbated or caused by a neurotraumatic event.

Neurotraumatic diseases/events as defined herein include both open or penetrating head trauma, such as caused by surgery, or a closed head trauma injury, such as caused by an injury to the head region. Also included within this definition is ischemic stroke, particularly to the brain area, transient ischemic attacks following coronary by-pass and cognitive decline following other transient ischemic conditions.

Ischemic stroke may be defined as a focal neurologic disorder that results from insufficient blood supply to a particular brain area, usually as a consequence of an embolus, thrombi, or local atheromatous closure of the blood vessel. Roles for stress stimuli (such as anoxia), redox injury, excessive neuronal excitatory stimulation and inflammatory cytokines in this area has been emerging and the present invention provides a means for the potential treatment of these injuries. Relatively little treatment, for an acute injury such as these has been available.

The compounds of the invention may also be used in the treatment or prophylaxis of cancers. It is suggested that the compounds are effective in tumors that have activating B-Raf mutations (V599E) as well as tumors that are activated by Ras mutation. Mutations may occur in the Ras family members such as Kras2 with mutation G13D. Furthermore compounds of the invention may be used in the treatment or prophylaxis of colorectal cancer and melanoma According to a further aspect of the invention there is provided a method of treatment or prophylaxis of a mammal who is suffering from or susceptible to cancer, which comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of cancers.

The compounds of formula (I) and pharmaceutically acceptable derivatives thereof, may be employed alone or in combination with other therapeutic agents for the treatment of the above-mentioned conditions. In particular, in anti-cancer therapy, combination with other chemotherapeutic, hormonal or antibody agents is envisaged as well as combination with surgical therapy and radiotherapy. Combination therapies according to the present invention thus comprise the administration of at least one compound of formula (I) or a pharmaceutically acceptable derivative thereof, and the use of at least one other cancer treatment method. Preferably, combination therapies according to the present invention comprise the administration of at least one compound of formula (I) or a pharmaceutically acceptable derivative thereof, and at least one other pharmaceutically active chemotherapeutic agent. These include existing and prospective chemotherapeutic agents. The compound(s) of formula (I) and the other pharmaceutically active chemotherapeutic agent(s) may be administered together in a unitary pharmaceutical composition or separately and, when administered separately this may occur simultaneously or sequentially in any order. Such sequential administration may be close in time or remote in time. The amounts of the compound(s) of formula (I) and the other pharmaceutically active chemotherapeutic agent(s) and the relative timings of administration will be selected in order to achieve the desired combined therapeutic effect.

Pharmaceutically active chemotherapeutic agents which can be useful in combination with a compound of formula (I) or a pharmaceutically acceptable derivative thereof, include but are not restricted to the following:

(1) cell cycle specific anti-neoplastic agents include, but are not limited to, diterpenoids such as paclitaxel and its analog docetaxel; tubulin poisons such as taxol/taxane or vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludarabine, methotrexate, cladrabine, cytarabine, mercaptopurine, gemcitabine, and thioguanine; and camptothecins such as 9-amino camptothecin, irinotecan, topotecan, and the various optical forms of 7-(4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, dacarbazine and nitrosoureas; anti-tumour antibiotics such as doxorubicin, daunomycin, epirubicin, idarubicin, mitomycin-C, dactinomycin, bleomycin and mithramycin; and platinum coordination complexes such as cisplatin, carboplatin, and oxaliplatin; and (3) other chemotherapeutic agents including, but not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; antiandrogens such as flutamide, nilutamide, bicalutamide, and cyproterone acetate; LHRH agonists and antagagonists such as goserelin acetate and luprolide, testosterone 5α-dihydroreductase inhibitors such as finasteride; metalloproteinase inhibitors such as marimastat; antiprogestrogens; mitoxantrone, 1-asparaginase, urokinase plasminogen activator receptor function inhibitors; inhibitors or c-kit and bcr/abl tyrosine kinases, (such as Gleevec), immunotherapy, immunoconjugates, cytokines (such as IL-2, IFN alpha and beta), tumor vaccines (including dendritic cell vaccines), thalidomide, COX-2 inhibitors, glucocorticoids (such as prednisone and decadron), radiation sensitizers, (such as temazolamide), growth factor function inhibitors such as inhibitors of the functions of hepatocyte growth factor; erb-B2, erb-B4, epidermal growth factor receptor (EGFR) and platelet derived growth factor receptors (PDGFR); inhibitors of angiogenesis such as inhibitors of the function of Ephrin receptors (such as, EphB4), vascular endothelial growth factor receptors (VEGFR) and the angiopoietin receptors (Tie1 and Tie2); and other kinase inhibitors such as inhibitors of CDK2 and CDK4.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

According to a further aspect of the invention there is provided a method of treatment or prophylaxis of chronic neurodegeneration, pain, migraine or cardiac hypertrophy, in a mammal in need thereof, which comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of chronic neurodegeneration, pain, migraine or cardiac hypertrophy.

In order to use the compounds of formula (I) in therapy, they will normally be formulated into a pharmaceutical composition in accordance with standard pharmaceutical practice.

According to a further aspect of the invention there is provided a pharmaceutical composition comprising a compound of formula (I) or a pharmaceutically acceptable derivative thereof and a pharmaceutically acceptable carrier.

The compounds of formula (I) may conveniently be administered by any of the routes conventionally used for drug administration, for instance, parenterally, orally, topically or by inhalation. The compounds of formula (I) may be administered in conventional dosage forms prepared by combining it with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier is dictated by the amount of compound of formula (I) with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampoule or nonaqueous liquid suspension.

The compounds of formula (I) are preferably administered parenterally, that is by intravenous, intramuscular, subcutaneous, sublingual, intranasal, intrarectal, intravaginal or intraperitoneal administration. The intravenous form of parenteral administration is generally preferred. The compounds may be administered as a bolus or continuous infusion e.g. of 6 hours up to 3 days. Appropriate dosage forms for such administration may be prepared by conventional techniques.

The compounds of formula (I) may also be administered orally. Appropriate dosage forms for such administration may be prepared by conventional techniques.

The compounds of formula (I) may also be administered by inhalation, that is by intranasal and oral inhalation administration. Appropriate dosage forms for such administration, such as aerosol formulations, may be prepared by conventional techniques.

The compounds of formula (I) may also be administered topically, that is by non-systemic administration. This includes the application of the inhibitors externally to the epidermis or the buccal cavity and the instillation of such a compound into the ear, eye and nose, such that the compound does not significantly enter the blood stream.

For all methods of use disclosed herein the daily oral dosage regimen will preferably be from about 0.1 to about 80 mg/kg of total body weight, preferably from about 0.2 to 30 mg/kg, more preferably from about 0.5 to 15 mg/kg. The daily parenteral dosage regimen about 0.1 to about 80 mg/kg of total body weight, preferably from about 0.2 to about 30 mg/kg, and more preferably from about 0.5 to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of the inhibitors will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of the inhibitors given per day for a defined number of days, can be ascertained by those skilled in the art using conventional course of treatment determination tests. In the case of pharmaceutically acceptable salts the above figures are calculated as the parent compound of formula (I).

No toxicological effects are indicated/expected when a compound of formula (I) is administered in the above mentioned dosage range.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention and the following Descriptions illustrate the preparation of intermediates used in the preparation of these compounds.

Abbreviations used herein are as follows;
THF means tetrahydrofuran.
DMF means N,N-Dimethylformamide.

Description 1: 1-Methoxyimino-indan-5-boronic acid

Step 1. 5-Bromoindan-1-one O-methyl oxime

To a solution of 5-bromoindan-1-one (100 g, 0.47 mol) in ethanol (650 ml) under argon was added methoxylamine hydrochloride (198 g, 2.38 mol) and pyridine (125 ml). The mixture was heated under reflux for 2.5 hours, cooled to room temperature and poured into saturated aqueous sodium hydrogen carbonate solution. The mixture was extracted with ethyl acetate and the organic phase dried and concentrated in vacuo. The crude material was recrystallised from isopropanol to afford the title compound (110 g, 97%); $^1$H NMR (CDCl$_3$) 7.52 (1H, d, J 8.3 Hz), 7.43 (1H, d, J 1 Hz), 7.35 (1H, dd, J 8.3, 1 Hz), 3.97 (3H, s), 2.99 (2H, m), 2.85 (2H, m).

Step 2. 1-Methoxyimino-indan-5-boronic acid

A solution of the product of Example 1 Step 1 (48.0 g, 0.2 mol) in tetrahydrofuran (1 L) at −78° C. under argon atmosphere was treated dropwise with n-butyl lithium (138 ml, 1.6M in hexanes, 0.22 mol). After stirring at −78° C. for 30 minutes trimethyl borate (49 ml, 0.44 mol) was added and the solution warmed to room temperature and stirred for 16 hours. The mixture was concentrated in vacuo, acidified to pH1 with 5N hydrochloric acid and stirred at room temperature for 1 hour. The mixture was then basified with 40% sodium hydroxide and the solution washed three times with diethyl ether. The aqueous phase was re-acidified to pH1 and the mixture was extracted five times with ethyl acetate. The organic extracts were combined washed with brine, dried and evaporated in vacuo. The residue was triturated with hexane, filtered, washed with hexane and then a small amount of ether to afford the title compound (23.6 g, 58%); MS(AP−) m/e 204 [M−H]−.

Description 2: 4-(1-Oxo-indan-5-yl)-5-pyridin4-yl-furan-2-carboxylic acid hydrochloride Step 1. 4-Bromo-5-pyridin-4-yl-furan-2-carboxylic acid tert-butyl ester tert-Butyl 4,5-dibromo-2-furancarboxylate (H. Muratake et al, *Chem. Pharm. Bull.*, 1997, 45, 799) (9.78 g, 30 mmol), 4-pyridyl boronic acid (M. Lamothe et al, *J. Med. Chem.*, 1997, 40, 3542) (4.06 g, 33 mmol), potassium carbonate (24.8 g, 180 mmol), triphenylphosphine (786 mg, 3 mmol) and palladium (II) acetate (337 mg, 1.5 mmol) were dissolved in ethylene glycol dimethyl ether (150 ml) and water (75 ml). The mixture was heated at reflux for 18 hours with vigorous stiring, cooled then filtered through celite pad, which was thoroughly washed with ethyl acetate. The filtrate was then washed with saturated sodium bicarbonate solution, water (×3) and brine, then dried over magnesium sulfate. The solution was evaporated in vacuo and the residue purified by silica gel chromatography to afford the title product (5.32 g, 55%); MS (AP−) m/e 323/325 [M−H]−.

Step 2. 4-(1-Methoxyimino-indan-5-yl)-5-pyridin-4-yl-furan-2-carboxylic acid tert-butyl ester The product of Step 1 (5.32 g, 16.4 mmol), the product of Description 1 (4.03 g, 19.7 mmol), potassium carbonate (13.6 g, 98.4 mmol), triphenylphosphine (365 mg, 1.64 mmol) and palladium acetate (184 mg, 0.8 mmol) were dissolved in ethylene glycol dimethyl ether (100 ml) and water (50 ml). The mixture was then heated under reflux for 5 hours, cooled and filtered through a pad of celite. The filtrate was then washed with saturated sodium bicarbonate solution, water and brine. The solution was dried over magnesium sulfate and evaporated in vacuo and the residue purified by silica gel chromatography eluting with a mixture of ethyl acetate/hexane (1:1) to afford the title product (4.74 g, 71%); MS (AP−) m/e 403 [M−H]−.

Step 3. 4-(1-Methoxyimino-indan-5-yl)-5-pyridin-4-yl-furan-2-carboxylic acid trifluoroacetic acid salt The product from Step 2 (4.74 g, 11.7 mmol) was dissolved in trifluoroacetic acid (50 ml) and dichloromethane (50 ml). The solution was stirred at room temperature for 3 hours and then evaporated in vacuo, azeotroping three times with dichloromethane. The resulting solid was triturated with diethyl ether, filtered and dried to afford the title product (5.46 g), which was used without further purification; MS (AP−) m/e 347 [M−H]−.

Step 4. 4-(1-Oxo-indan-5-yl)-5-pyridin-4-yl-furan-2-carboxylic acid hydrochloride salt The product from Step 3 (5.46 g, 11.7 mmol) was suspended in 5M hydrochloric acid (50 ml), dioxane (50 ml) and acetone (10 ml). The suspension was heated to reflux for 30 minutes, whereupon the suspended solids dissolved. The heating was continued for a further 90 minutes before the mixture was cooled, diluted with acetone (100 ml) and evaporated in vacuo to a wet solid. The solid was dried by repeatedly (×3) suspending in toluene and evaporating to dryness.

The residue was then triturated with diethyl ether, filtered and dried in vacuo to afford the title compound (4.10 g, 97%); MS (ES+) m/e 320 [M+H]+.

Description 3: 5-(Oxo-indan-5-yl)-4pyridin-4-yl-furan-2-carboxylic acid hydrochloride Step 1. 4Bromo-5-(1-methoxyimino-indan-5-yl)-furan-2-carboxylic acid tert-butyl ester The title compound (5.83 g, 46%) was prepared from tert-butyl 4,5-dibromo-2-furancarboxylate (H. Muratake et al, Chem. Pharm. Bull., 1997, 45, 799), (10.104 g, 30.99 mmol) and the product from Description 1 Step 2 (6.355 g, 30.99 mmol) by the general procedure of Description 2 Step 1; MS (AP+ve) m/e 406/408 [M+H]+.

Step 2. 5-(1-Methoxyimino-indan-5-yl-4-pyridin-4-yl-furan-2-carboxylic acid tert-butyl ester 4-Tributylstannyl pyridine (13.659 g, 37.11 mmol) and dichlorobis (triphenylphosphine)palladium II (3.472 g, 4.948 mmol) were added to a solution of the product from Step1 (10.05 g, 24.737 mmol), in toluene (100 ml) and the mixture heated under reflux for 4 days. The reaction was then cooled and filtered through a pad of celite, and washed thoroughly with ethyl acetate. The organics were washed with saturated sodium bicarbonate solution, water (×3) and brine, dried over anhydrous magnesium sulfate and then evaporated in vacuo. The crude residue was chromatographed on silica gel eluting with a mixture of ethyl acetate/hexane (1:1) to afford the title compound (6.82 g, 68%); MS (AP+ve) m/e 405 [M+H]+.

Step 3. 5-(1-Oxo-indan-5-yl)-4-pyridin-4-yl-furan-2-carboxylic acid hydrochloride salt The title compound (2.32 g, 84%) was prepared from the product from step 2 (3.17 g, 7.83 mmol) by the general 2 step method of description 2, steps 3 and 4; MS (ES+) m/e 320 [M+H]+.

EXAMPLE 1

5-[5-(1-Morpholin-4-yl-methanoyl)-2-pyridin-4-yl-furan-3-yl]-indan-1-one oxime

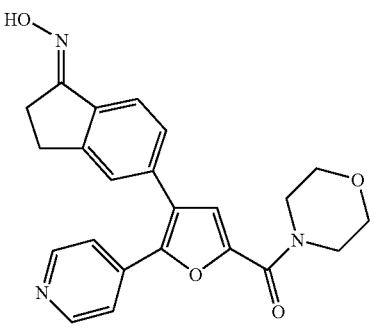

Step 1. 5-{5-(1-Morpholin-4-yl-methanoyl)-2-pyridin-4-yl-furan-3-yl]-indan-1-one The product of Description 2 (178 mg, 0.5 mmol), N-cyclohexylcarbodiimide,N'-methyl polystyrene resin (1.8 mmol/g) (555 mg, 1 mmol), and 1-hydroxybenzotriazole hydrate (135 mg, 1 mmol) were suspended in DMF (5 ml) and then treated with triethylamine (0.083 ml, 0.6 mmol) and morpholine (0.053 ml, 0.6 mmol). The reaction was stirred at room temperature for 16 hours and applied to a 10 g SCX cartridge (Varian Mega Bond Elute). The cartridge was washed with methanol and then a mixture of 0.880 ammonia/methanol (1:9) solution. The product containing fractions were combined, evaporated in vacuo and the residue purified by silica gel chromatography eluting with a mixture of 0.880 ammonia/ethanol/dichloromethane (1:9:90) to afford the title compound (137 mg, 71%); MS (ES+) m/e 389 (M+H)+.

Step 2. 5-[5-(1-Morpholin-4-yl-methanoyl)-2-pyridin-4-yl-furan-3-yl]-indan-1-one oxime The product from Step 1 (137 mg, 0.35 mmol) was dissolved in ethanol (10 ml) and treated with hydroxylamine (1 ml, 50% aqueous solution) and the solution heated to reflux for 1 hour. After cooling, the reaction mixture was concentrated and the residue triturated with diethyl ether, filtered and the solid dried in vacuo. Purification of the solid by silica gel chromatography eluting with a mixture of 0.880 ammonia/ethanol/dichloromethane (1:9:90) afforded the title compound (43 mg, 30%); MS (ES+) m/e 404 (M+H)+.

The following examples were prepared by the general two-step method described in Example 1.

| Example | Amine | Characterisation |
|---|---|---|
| 2 5-[5-(1-Piperidin-1-yl-methanoyl)-2-pyridin-4-yl-furan-3-yl]-indan-1-one oxime | piperidine | MS(AP+) m/e 402 [M + H]+ |
| 3 4-(1-Hydroxyimino-indan-5-yl)-5-pyridin-4-yl-furan-2-carboxylic acid (2-morpholin-4-yl-ethyl)-amide | 4-(2-aminoethyl)morpholine | MS(AP+) m/e 447 [M + H]+ |
| 4 5-(5-{1-[4-(2-Methoxy-ethyl)-piperazin-1-yl]-methanoyl}-2-pyridin-4-yl-furan-3-yl)-indan-1-one oxime | 1-(2-methoxy-ethyl)-piperazine, (Kazunori et al., Chem. Pharm. Bull. 1993, 41,148) | MS(AP+) m/e 461 [M + H]+ |
| 5 4-(1-Hydroximino-indan-5-yl)-5-pyridin-4-yl-furan-2-carboxylic acid methyl-(1-methyl-piperidin-4-yl)-amide | 1-methyl-4-(methylamino)piperidine | MS(ES+) m/e 445 [M + H]+ |
| 6 5-[5-(1-[1,4']Bipiperidinyl-1'-yl-methanoyl)-2-pyridin-4-yl-furan-3-yl]-indan-1-one oxime | 4-piperidinopiperidine | MS(ES+) m/e 485 [M + H]+ |
| 7 5-(5-{1-[4-(4-Chloro-benzyl)-piperazin-1-yl]-methanoyl}-2-pyridin-4-yl-furan-3-yl)-indan-1-one oxime | 1-(4-chlorobenzyl)-piperazine | MS(ES+) m/e 527/529 [M + H]+ |
| 8 5-{5-[1-(4-Cyclohexyl-piperazin-1-yl)-methanoyl]-2-pyridin-4-yl-furan-3-yl}-indan-1-one oxime | 1-cyclohexylpiperazine | MS(ES+) m/e 485 [M + H]+ |
| 9 5-{5-[1-(4-Methyl-piperazin-1-yl)-methanoyl]-2-pyridin-4-yl-furan-3-yl}-indan-1-one oxime | 1-methylpiperazine | MS(ES+) m/e 417 [M + H]+ |
| 10 5-(5-{1-[4-(2-Oxo-2-pyrrolidin-1-yl-ethyl)-piperazin-1-yl]methanoyl}-2-pyridin-4-yl-furan-3-yl)-indan-1-one oxime | 1-(2-(piperazin-1-yl)-acetyl)-pyrrolidine | MS(ES+) m/e 514 [M + H]+ |
| 11 4-(1-Hydroxyimino-indan-5-yl)-5-pyridin-4-yl-furan-2-carboxylic acid 4-dimethyamino-benzylamide | 4-dimethylaminobenzylamine | MS(ES+) m/e 467 [M + H]+ |
| 12 4-(1-Hydroxyimino-indan-5-yl)-5-pyridin-4-yl-furan-2-carboxylic acid (2-dimethylaminoethyl)-methylamide | N,N,N'-trimethylethylenediamine | MS(ES+) m/e 419 [M + H]+ |
| 13 4-[({1-[4-(1-Hydroxyimino-indan-5-yl)-5-pyridin-4-yl-furan-2-yl]-methanoyl}-amino)-methyl]-piperidine-1-carboxylic acid tert-butyl ester | tert-butyl-4-(aminomethyl)-tetrahydropyridin-1-(2H)-carboxylate | MS(AP+) m/e 531 [M + H]+ |
| 14 4-(1-Hydroxyimino-indan-5-yl)-5-pyridin-4-yl-furan-2-carboxylic acid (2-dimethylamino-ethyl)-amide | N,N-dimethlyethylene diamine | MS(AP+) m/e 405 [M + H]+ |
| 15 5-(2-Pyridin-4-yl-5-{1-[4-(2-pyrrolidin-1-yl-ethyl)-piperazin-1-yl]-methanoyl}-furan-3-yl)-indan-1-one oxime | 1-(2-(1-pyrrolidyl)-ethyl)-piperazine | MS(AP+) m/e 500 [M + H]+ |
| 16 4-(1-Hydroxyimino-indan-5-yl)-5-pyridin-4-yl-furan-2-carboxylic acid (1-piperidin-4-yl-cyclohexylmethyl)-amide | (1-piperidin-1-yl-cyclohexyl)-methylamine | MS(AP+) m/e 513 [M + H]+ |
| 17 4(1-Hydroxyimino-indan-5-yl)-5-pyridin-4-yl-furan-2-carboxylic acid [4-(2-dimethyl amino-ethoxy)-phenyl]-amide | 4-(2-dimethylamino-ethoxy) phenylamine. (Paul et al., J. Med. Chem., 1993, 36(19), 2716) | MS(AP+) m/e 497 [M + H]+ |
| 18 4-(1-Hydroxyimino-indan-5-yl)-5-pyridin-4-yl-furan-2-carboxylic acid (2-pyrrolidin-1-yl-ethyl)-amide | N-(2-aminoethyl)-pyrrolidine | MS(AP+) m/e 431 [M + H]+ |
| 19 4-(1-Hydroxyimino-indan-5-yl)-5-pyridin-4-yl-furan-2-carboxylic acid [3-(4-methyl-piperazin-1-yl)-propyl]-amide | 1-(3-aminopropyl)-4-methylpiperazine | MS(AP+) m/e 474 [M + H]+ |
| 20 5-{2-Pyridin-4-yl-5-[1-(4-pyrrolidin-1-yl-piperidin-1-yl)-methanoyl}-furan-3-yl}-indan-1-one oxime | 4-pyrrolidinopiperidine | MS(AP+) m/e 471 [M + H]+ |

| Example | Amine | Characterisation |
|---|---|---|
| 21 5-(5-{1-[4-(2-Dimethylaminoethyl)-piperazin-1-yl]-methanoyl}-2-pyridin-4-yl-furan-3-yl)-indan-1-one oxime | 1-(2-aminomethyl)piperidine | MS(AP+) m/e 445 [M + H]+ |
| 22 5-(5-{1-[4-(2-Dimethylaminoethyl)-piperazin-1-yl]-methanoyl}-2-pyridin-4-yl-furan-3-yl)-indan-1-one oxime | 1-(2-dimethylaminoethyl)-piperazine | MS(AP+) m/e 474 [M + H]+ |
| 23 4-(1-Hydroxyimino-indan-5-yl)-5-pyridin-4-yl-furan-2-carboxylic acid (2-diisopropyl amino-ethyl)-amide | N,N-diisopropylethylene diamine | MS(AP+) m/e 461 [M + H]+ |
| 24 4-(1-Hydroxyimino-indan-5-yl)-5-pyridin-4-yl-furan-2-carboxylic acid ((1R,5S)-8-methyl-8-azabicyclo[3.2.1]oct-3-yl)amide | (1R,5S)-8-methyl-8-azabicyclo[3.2.1]oct-3-yl amine | MS(AP+) m/e 456 [M + H]+ |
| 25 4-(1-Hydroximino-indan-5-yl)-5-pyridin-4-yl-furan-2-carboxylic acid ((1R,5S)-9-methyl-9-azabicyclo[3.3.1]non-3-yl)amide | ((1R,5S)-9-methyl-9-azabicyclo[3.3.1]non-3-yl) amine. (Bermundez et al., J. Med. Chem., 1990, 33, 7 1924) | MS(AP+) m/e 471 [M + H]+ |

EXAMPLE 26

4-(1-Hydroxyimino-indan-5-yl)-5-pyridin-4-yl-furan-2-carboxylic acid methyl-piperidin-4-yl-amide

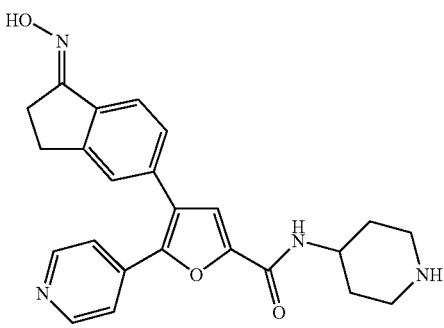

Step 1. 4-({1-[4-(1-Oxo-indan-5-yl)-5-pyridin-4-yl-furan-2-yl]-methanoyl}-amino)-piperidine-1-carboxylic acid tert-butyl ester The title compound (122 mg, 49%) was obtained from the product from Description 2 (178 mg, 0.5 mmol) and 4-amino-piperidine-1-carboxylic acid tert-butyl ester (110 mg, 0.55 mmol) by the general method of example 1 step 1; MS (ES+) m/e 389 (M+H)+.

Step 2. 4-(1-Hydroxyimino-indan-5-yl)-5-pyridin-4-yl-furan-2-carboxylic acid methyl-piperidin-4-yl-amide The product from Step 1 (122 mg, 0.24 mmol) was stirred in trifluoroacetic acid (5 ml) and dichloromethane (5 ml) at room temperature for 2 hours and the solution was then co-evaporated three times with dichloromethane. The resulting residue was treated according to the general method of Example 1 Step 2 to give the title compound (0.02 g, 20%); MS (AP+) m/e 416 (M+H)+.

The following examples were prepared by the general method described in Example 26.

| Example | Amine | Characterisation |
|---|---|---|
| 27 5-[5-(1-Piperazin-1-yl-methanoyl)-2-pyridin-4-yl)-furan 3-yl]-indan-1-one oxime | tert-butyl 1-piperazine carboxylate | MS(AP+) m/e 403 [M + H]+ |
| 28 4-(1-Hydroxyimino-indan-5-yl)-5-pyridin-4-yl-furan-2-carboxylic acid methyl-piperidin-4-yl-amide | 1-tert-butoxycarbonyl-4-methylaminopiperidine PCT Int. Appl (1999) WO 9964394 | MS(AP+) m/e 431 [M + H]+ |

EXAMPLE 29

5-(1-Hydroxyimino-indan-5-yl)-4-pyridin-4-yl-furan-2-carboxylic acid (2-dimethylamino-ethyl)-methyl-amide

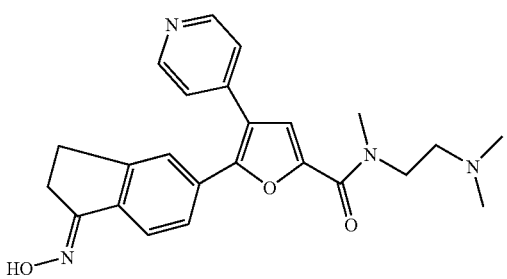

Step 1. 5-(1-Oxo-indan-5-yl)-4-pyridin-4-yl-furan-2-carboxylic acid (2-dimethylamino-ethyl)-methyl-amide The product from Description 3 (200 mg, 0.562 mmol), N-cyclohexylcarbodiimide N'-methyl polystyrene resin (1.8 mmol/g) (938 mg, 1.686 mmol), and 1-hydroxybenzotriazole hydrate (228 mg, 1.686 mmol) were suspended in dimethylformamide (5 ml) and dichloromethane (3 ml) and treated with triethylamine (58 mg, 0.562 mmol) and N,N,N-trimethylethlenediamine (172 mg, 1.686 mmol). The reaction was stirred at room temperature for 16 hours and then applied to a 10 g SCX cartridge (Varian Mega Bond Elute). The cartridge was washed with methanol and then a mixture of 0.880 ammonia/methanol (1:10). The product containing fractions were combined, evaporated in vacuo, and the residue chromatographed on silica gel eluting with a mixture of 0.880 ammonia/methanol/dichloromethane (1:9:90) to afford the title compound (180 mg, 80%); MS (AP+) m/e 404 (M+H)$^+$.

Step 2. 5-(1-Hydroxyimino-indan-5-yl)-4-pyridin-4-yl-furan-2-carboxylic acid (2-dimethylamino-ethyl)-methyl-amide The title compound (110 mg, 59%) was prepared from the product of Step 1 using the method of Example 1 Step 2; MS (AP+ve): m/e 419 (M+H)$^+$.

The following examples were prepared by the general two-step method described in Example 29. Varying quantities of triethylamine were added to the reactions in Step 1 as indicated:

| Example | | Amine | Et$_3$N | Characterisation |
|---|---|---|---|---|
| 30 | 5-(1-Hydroxyimino-5-yl)-4-pyridin-4-yl-furan-2-carboxylic acid methyl-(1-methyl-piperidin-4-yl)-amide | 1-methyl-4-(methylamino)piperidine | 1 equivalent | MS(AP+) m/z 445 [M + H]$^+$ |
| 31 | 5-[5-(1-[1,4']Bipiperidinyl-1'-yl-methanoyl)-3-pyridin-4-yl-furan-2-yl]-indan-1-one oxime | 4-piperidinopiperidine | 1 equivalent | MS(AP+) m/z 485 [M + H]$^+$ |
| 32 | 5-(5-{1-[4-(4-Chloro-benzyl)-piperazin-1-yl]-methanoyl}-3-pyridin-4-yl-furan-2-yl)-indan-1-one oxime | 1-(4-chlorobenzyl)-piperazine | 0 equivalent | MS(AP+) m/z 527/529 [M + H]$^+$ |
| 33 | 5-{5-[1-(4-Cyclohexyl-piperazin-1-yl)-methanoyl]-3-pyridin-4-yl-furan-2-yl}-indan-1-one oxime | 1-cyclohexylpiperazine | 0 equivalent | MS(ES+) m/e 485 [M + H]$^+$ |
| 34 | 5-{5-[1-(4-Methyl-piperazin-1-yl)-methanoyl]-3-pyridin-4-yl-furan-2-yl}-indan-1-one oxime | 1-methylpiperazine | 0 equivalent | MS(ES+) m/e 417 [M + H]$^+$ |
| 35 | 5-(1-Hydroxyimino-indan-5-yl)-4-pyridin-4-yl-furan-2-carboxylic acid (2-pyrrolidin-1-yl-ethyl)-amide | 1-aminoethylpyrrolidine | 0 equivalent | MS(ES+) m/e 431 [M + H]$^+$ |
| 36 | 5-(5-{1-[4-(2-Oxo-2-pyrrolidin-1-yl-ethyl)-piperazin-1-yl]-methanoyl}-3-pyridin-4-yl-furan-2-yl)-indan-1-one oxime | 1-(2-(piperazin-1-yl)-acetyl)-pyrrolidine | 0 equivalent | MS(ES+) m/e 514 [M + H]$^+$ |
| 37 | 5-(1-Hydroxyimino-indan-5-yl)-4-pyridin-4-yl-furan-2-carboxylic acid 4-dimethylamino-benzylamide | 4-dimethylamino benzylamine | 2 equivalents | MS(ES+) m/e 467 [M + H]$^+$ |

EXAMPLE 38

5-(1-Hydroxyimino-indan-5-yl)-4-pyridin-4-yl-furan-2-carboxylic acid (2-diisopropylamino-ethyl)-amide

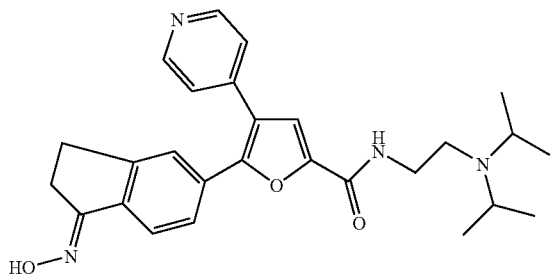

Step 1. 5-(1-Oxo-indan-5-yl)-4-pyridin-4-yl-furan-2-carboxylic acid (2-diisopropylamino-ethyl)-amide The product from Description 3 (250 mg, 0.703 mmol), N-cyclohexylcarbodiimide N'-methyl polystyrene resin (1.7 mmol/g) (1.240 g, 2.190 mmol) and 1-hydroxybenzotriazole hydrate (104 mg, 0.773 mmol) were suspended in tetrahydrofuran (7 ml) and dichloromethane (3 ml) and treated with triethylamine (78 mg, 0.773 mmol) and N,N,diisopropylethylene diamine (122 mg, 0.846 mmol). The reaction was stirred at room temperature for 16 hours, filtered and the filtrate evaporated in vacuo and the residue chromatographed on silica gel eluting with a mixture of 0.880 ammonia/methanol/dichloromethane (1/9/90) to afford the title compound (187 mg, 60%); MS (ES+) m/e 446 (M+H)$^+$.

Step 2. 5-(1-Hydroxyimino-indan-5-yl)-4-pyridin-4-yl-furan-2-carboxylic acid (2-dimethylamino-ethyl)-methyl-amide The title compound (0.051 g, 26%) was prepared from the product of Step 1 using the method of Example 1 Step 2; MS (AP+ve): m/e 461 (M+H)$^+$.

The following examples were prepared by the general two step method as described in example 38.

| | Example | Amine | Characterisation |
|---|---|---|---|
| 39A | 5-(1-Hydroxyimino-indan-5-yl)-4-pyridin-4-yl-furan-2-carboxylic acid (2-diisopropylamino-ethyl)-amide | $N^1,N^1$-Diisopropyl-ethane-1,2-diamine | MS(ES+) m/e 461 [M + H]$^+$ |
| 39B | 4-[({1-[5-(1-Hydroxyimino-indan-5-yl)-4-pyridin-4-yl-furan-2-yl]-methanoyl}-amino)-methyl]-piperidine-1-carboxylic acid tert-butyl ester | 4-Aminomethyl-piperidine-1-carboxylic acid tert-butyl ester | MS(ES+) m/e 531 [M + H]$^+$ |
| 40 | 5-(3-Pyridin-4-yl-5-{1-[4-(2-pyrrolidin-1-yl-ethyl)-piperazin-1-yl]-methanoyl}-furan-2-yl)-indan-1-one oxime | 1-(2-Pyrrolidin-1-yl-ethyl)-piperazine | MS(ES+) m/e 500 [M + H]$^+$ |
| 41 | 5-(1-Hydroxyimino-indan-5-yl)-4-pyridin-4-yl-furan-2-carboxylic acid (2-hydroxy-ethyl)-amide | 2-Amino-ethanol | MS(ES+) m/e 378 [M + H]$^+$ |
| 42 | 5-(1-Hydroxyimino-indan-5-yl)-4-pyridin-4-yl-furan-2-carboxylic acid (2-pyrrolidin-1-yl-ethyl)-amide | 2-Pyrrolidin-1-yl-ethylamine | MS(ES+) m/e 431 [M + H]$^+$ |
| 43 | 5-(1-Hydroxyimino-indan-5-yl)-4-pyridin-4-yl-furan-2-carboxylic acid (2-dimethylamino-ethyl)-amide | $N^1,N^1$-Dimethyl-ethane-1,2-diamine | MS(ES+) m/e 405 [M + H]$^+$ |
| 44 | 5-(1-Hydroxyimino-indan-5-yl)-4-pyridin4-yl-furan-2-carboxylic acid [3-(4-methyl-piperazin-1-yl)-propyl]-amide | 3-(4-Methyl-piperazin-1-yl)-propylamine | MS(ES+) m/e 474 [M + H]$^+$ |
| 45 | 5-(1-Hydroxyimino-indan-5-yl)-4-pyridin-4-yl-furan-2-carboxylic acid (1-piperidin-1-yl-cyclohexylmethyl)-amide | C-(1-Piperidin-1-yl-cyclohexyl)-methylamine | MS(ES+) m/e 513 [M + H]$^+$ |
| 46 | 5-(1-Hydroxyimino-indan-5-yl)-4-pyridin-4-yl-furan-2-carboxylic acid [4-(2-dimethylamino-ethoxy)-phenyl]-amide | 4-(2-Dimethylamino-ethoxy)-phenylamine | MS(ES+) m/e 497 [M + H]$^+$ |

-continued

| Example | | Amine | Characterisation |
|---|---|---|---|
| 47 | 5-(1-Hydroxyimino-indan-5-yl)-4-pyridin-4-yl-furan-2-carboxylic acid (3-dimethylamino-propyl)-amide | N¹,N¹-Dimethyl-propane-1,3-diamine | MS(ES+) m/e 419 [M + H]⁺ |
| 48 | 5-(1-Hydroxyimino-indan-5-yl)-4-pyridin-4-yl-furan-2-carboxylic acid (2-piperidin-1-yl-ethyl-amide | 2-Piperidin-1-yl-ethylamine | MS(ES+) m/e 445 [M + H]⁺ |

EXAMPLE 49

5-(1-Hydroxyimino-indan-5-yl)-4-pyridin-4-yl-furan-2-carboxylic acid (2-amino-ethyl)-amide

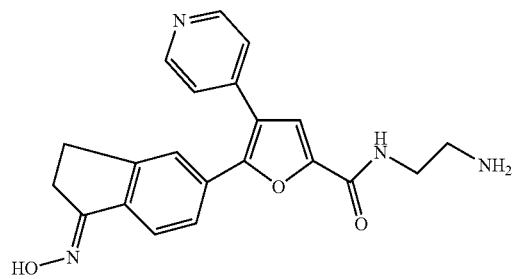

Step 1: 5-(1-Oxo-indan-5-yl)-4-pyridin-4-yl-furan-2-carboxylic acid (2-amino-ethyl)-amide The title compound (0.107 g, 33%) was prepared from the product of Description 3 (0.25 g, 0.703 mmol) and (2-amino-ethyl)-carbamic acid tert-butyl ester (135 mg, 0.843 mmol) using the method of Example 38 Step 1; MS (AP+) m/e 462 (M+H)⁺.

Step 2: 5-(1-Hydroxyimino-indan-5-yl)-4-pyridin-4-yl-furan-2-carboxylic acid (2-amino-ethyl)-amide The title compound (0.037 g, 23%) was prepared from the product of Step 1 using the method of Example 26 Step 2; MS (ES–ve): m/e 375 [M–H]⁻.

The following compounds were prepared by the general two step method as described in Example 49.

| Example | | Amine | Characterisation |
|---|---|---|---|
| 50 | 5-(1-Hydroxyimino-indan-5-yl)-4-pyridin-4-yl-furan-2-carboxylic acid piperidin-4-ylamide | 4-Amino-piperidine-1-carboxylic acid tert-butyl ester | MS(ES+) m/e 417 [M + H]⁺ |
| 51 | (+/−) 5-(1-Hydroxyimino-indan-5-yl)-4-pyridin-4-yl-furan-2-carboxylic acid pyrrolidin-3-ylamide | (+/−) 3-Amino-pyrrolidine-1-carboxylic acid tert-butyl ester | MS(ES+) m/e 403 [M + H]⁺ |

EXAMPLE 52

5-(1-Hydroximino-indan-5-yl)-4-pyridin-4-yl-thiophene-2-carboxylic acid methyl-(1-methyl-piperidin-4-yl)-amide

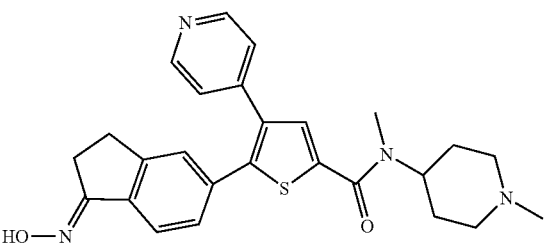

Step 1. 4,5-Dibromo-thiophene-2-carboxylic acid methyl-(1-methyl-piperidin-4-yl)-amide 4,5-Dibromothiophene-2-carboxylic acid (2.86 g, 10 mmol) was dissolved in dichloromethane (50 ml) and treated dropwise at 0° C. with oxalyl chloride (2.61 ml, 30 mmol). N,N-Dimethylfomamide (5 drops) was added and the solution stirred at room temperature for 3 hours. The solution was evaporated in vacuo and co-evaporated with dichloromethane (×3) to afford crude acid chloride, 3.04 g. The solid was dissolved in THF (10 ml) and treated with a solution of 1-methyl-4-(methylamino)piperidine (1.28 g, 10 mmol) and triethylamine (1.21 g, 12 mmol) in THF (20 ml). The mixture was stirred at room temperature for 16 hours, evaporated in vacuo and the residue partitioned between ethyl acetate and saturated sodium bicarbonate solution. The organic layer was washed three times with water, then brine, dried over magnesium sulfate and evaporated in vacuo to afford the title product (3.41 g, 90%) which was used without further purification; MS (ES+) m/e 397/399/401 [M+H]$^+$ Step 2. 4-Bromo-5-(1-methoxyimino-indan-5-yl)-thiophene-2-carboxylic acid methyl-(1-methyl-piperidin-4-yl)-amide The product of Step 1 (3.41 g, 9 mmol), the product of Description 1 (1.85 g, 9 mmol), potassium carbonate (7.46 g, 54 mmol), triphenylphosphine (240 mg, 0.9 mmol), and palladium acetate (100 mg, 0.45 mmol) were dissolved in ethylene glycol dimethyl ether (50 ml) and water (25 ml). The biphasic solution was heated at reflux for 36 hours, with vigorous stirring, cooled, then filtered through a pad of celite, which was thoroughly washed with ethyl acetate. The two phase filtrate was separated and the organic phase washed with saturated sodium bicarbonate solution, water (×3) and brine. The solution was dried over magnesium sulfate and evaporated in vacuo to a crude solid (4.9 g), which was purified by silica gel chromatography (1:9:90 0.880 ammonia:ethanol:dichloromethane), to afford the title product, (670 mg, 16%); MS (AP+) m/e 477/479 [M+H]$^+$ Step 3. 5-(1-methoxyimino-indan-5-yl)-4-pyridin-4-yl-thiophene-2-carboxylic acid methyl-(1-methyl-piperidin-4-yl)-amide The product of Step 2 (670 mg, 1.4 mmol), 4-pyridyl boronic acid (M. Lamothe et al *J. Med. Chem.*, 1997, 40, 3542) (189 mg, 1.5 mmol), potassium carbonate (1.17 g, 8.5 mmol), triphenylphosphine (37 mg, 0.14 mmol), and palladium acetate (16 mg, 0.07 mmol) were dissolved in ethylene glycol dimethyl ether (15 ml) and water (5 ml). The biphasic solution was heated at reflux for 16 hours, with vigorous stirring, cooled, then filtered through a pad of celite, which was thoroughly washed with ethyl acetate. The two phase filtrate was separated and the organic phase washed with saturated sodium bicarbonate solution, water (×3) and brine. The solution was dried over magnesium sulfate and evaporated in vacuo to a crude solid (691 mg), which was purified by silica gel chromatography (1:9:90 0.880 ammonia:ethanol:dichloromethane), to afford the title product, (476 mg, 72%); MS (AP+) m/e 475 [M+H]$^+$ Step 4. 5-(1-Oxo-indan-5-yl)-4-pyridin-4-yl-thiophene-2-carboxylic acid methyl-(1-methyl-piperidin-4-yl)-amide The product of step 3 (476 mg 1 mmol) was dissolved in 5N hydrochloric acid (10 ml), dioxane (10 ml) and acetone (5 ml) and heated at 80° C. for 2 hours. The resulting solution was concentrated in vacuo and co-evaporated with ethanol (×3) to afford a crude solid. This was partitioned between saturated sodium bicarbonate solution and ethyl acetate. The aqueous phase was re-extracted with ethyl acetate (×2), and the combined organic extracts were washed with water (×3), brine, dried and evaporated in vacuo to a crude solid. This was purified by column chromatography (1:9:40 0.880 ammonia:thanol:dichloromethane) to afford title product (300 mg, 67%); MS (AP+) m/e 446 [M+H]$^+$ Step 5. 5-(1-Hydroximino-indan-5-yl)-4-pyridin-4-yl-thiophene-2-carboxylic acid methyl-(1-methyl-piperidin-4-yl)-amide The product of step 4 (300 mg, 0.8 mmol) was heated at reflux in ethanol (10 ml) containing hydroxylamine (50% aqueous solution) (1 ml) for 1 hour. The solution was co-evaporated in ethanol (×3) to afford a crude solid. The product was purified twice by silica gel chromatography (1:9:40 0.880 ammonia:thanol:dichloromethane) to afford the title compound (80 mg, 22%); MS (AP+) m/e 461 [M+H]$^+$ It is to be understood that the present invention covers all combinations of particular and preferred subgroups described hereinabove.

BIOLOGICAL EXAMPLES

The activity of compounds of formula (I) as B-Raf inhibitors may be determined by the following in vitro assay:

Fluorescence Anisotropy Kinase Binding Assay

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×Ki) of a potent inhibitor the anisotropy of the unbound fluorescent ligand is measurably different from the bound value. The concentration of kinase enzyme should preferably be $\geq 1 \times K_f$. The concentration of fluorescent ligand required will depend on the instrumentation used, and the fluorescent and physicochemical properties. The concentration used must be lower than the concentration of kinase enzyme, and preferably less than half the kinase enzyme concentration. A typical protocol is:

All compounds are serially diluted in DMSO, then by a one step dilution into buffer of comparison, 50 mM HEPES, pharmaceutical pH7.5, 1 mM CHAPS, 10 mM $MgCL_2$, for the assay.

B-Raf Enzyme concentration: 1 nM

Fluorescent ligand concentration: 0.5 nM

Test compound concentration: 0.5 nM-100 uM

Components incubated in 10 ul final volume in LJL HE 384 type B black microtitre plate until equilibrium reached (Over 3 h, up to 30 h)

Fluorescence anisotropy read in an LJL Acquest fluorescence reader.

Definitions:

Ki=dissociation constant for inhibitor binding

Kf=dissociation constant for fluorescent ligand binding

The fluorescent ligand is the following compound:

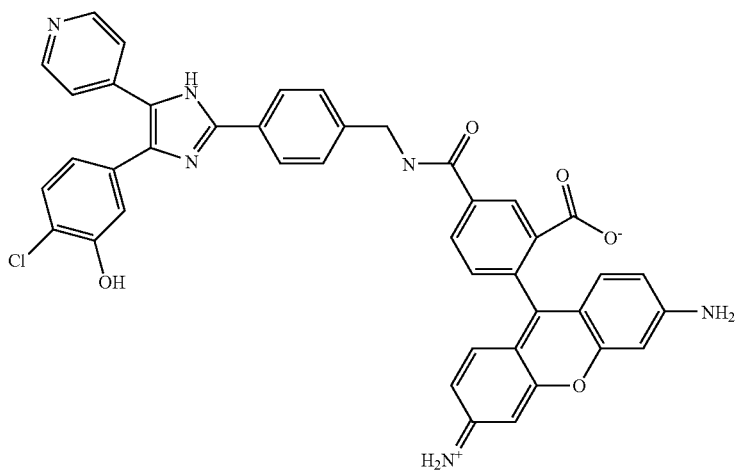

which is derived from 5-[2-(4-aminomethylphenyl)-5-pyridin-4-yl-1H-imidazol-4-yl]-2-chlorophenol and rhodamine green.

Compounds of the invention have a $K_d$ of less than 1 μM.

Raf Kinase Assay

Activity of human recombinant B-Raf protein was assessed in vitro by assay of the incorporation of radiolabelled phosphate to recombinant MAP kinase kinase (MEK), a known physiologic substrate of B-Raf. Catalytically active human recombinant B-Raf protein was obtained by purification from Sf9 insect cells infected with a human B-Raf recombinant baculovirus expression vector. To ensure that all substrate phosphorylation resulted from B-Raf activity, a catalytically inactive form of MEK was utilised. This protein was purified from bacterial cells expressing mutant inactive MEK as a fusion protein with glutathione-S-transferase (GST-kdMEK).

Method: Standard assay conditions of B-Raf catalytic activity utilised 3 ug of GST-kdMEK, 10 uM ATP and 2 uCi $^{33}$P-ATP, 50 mM MOPS, 0.1 mM EDTA, 0.1M sucrose, 10 mM $MgCl_2$ plus 0.1% dimethylsulphoxide (containing compound where appropriate) in a total reaction volume of 30 ul. Reactions were incubated at 25° C. for 90 minutes and reactions terminated by addition of EDTA to a final concentration of 50 uM. 10 ul of reaction was spotted to P81 phosphocellulose paper and air dried. Following four washes in ice cold 10% trichloroacetic acid, 0.5% phosphoric acid, papers were air dried prior to addition of liquid scintillant and measurement of radioactvity in a scintillation counter.

Results: The compounds of the examples were found to be effective in inhibiting B-Raf mediated phosphorylation of GST-kdMEK substrate having $IC_{50}$'s of <3 μM. The activity of compounds as Raf inhibitors may also be determined by the assays described in WO 99/10325; McDonald, O. B., Chen, W. J., Ellis, B., Hoffman, C., Overton, L., Rink, M., Smith, A., Marshall, C. J. and Wood, E. R. (1999) A scintillation proximity assay for the RafEK/ERK kinase cascade: high throughput screening and identification of selective enzyme inhibitors, Anal. Biochem. 268: 318-329 and AACR meeting New Orleans 1998 Poster 3793.

The neuroprotective properties of B-Raf inhibitors may be determined by the following in vitro assay:

Neuroprotective Properties of B-Raf Inhibitors in Rat Hippocampal Slice Cultures Organotypic cultures provide an intermediate between dissociated neuronal cell cultures and in-vivo models of oxygen and glucose deprivation (OGD). The majority of glial-neuronal interactions and neuronal circuitry are maintained in cultured hippocampal slices, so facilitating investigation of the patterns of death among differing cell types in a model that resembles the in vivo situation. These cultures allow the study of delayed cellular damage and death 24 hours, or more, post-insult and permit assessment of the consequences of long-term alterations in culture conditions. A number of laboratories have reported delayed neuronal damage in response to OGD in organotypic cultures of the hippocampus (Vornov et al., Stroke, 1994, 25, 57-465; Newell et al., Brain Res., 1995, 676, 38-44). Several classes of compounds have been shown to protect in this model, including EAA antagonists (Strasser et al., Brain Res., 1995, 687, 167-174), Na channel blockers (Tasker et al., J. Neurosci., 1992, 12, 98-4308) and Ca channel blockers (Pringle et al., Stroke, 1996, 7, 2124-2130). To date, relatively little is known of the roles of intracellular kinase mediated signalling pathways in neuronal cell death in this model.

Method: Organotypic hippocampal slice cultures were prepared using the method of Stoppini et al., J. Neurosci. Methods, 1995, 37, 173-182. Briefly, 400 micron sections prepared from hippocampi of 7-8 day postnatal Sprague Dawley rats are cultured on semiporous membranes for 9-12 days. OGD is then induced by incubation in serum and glucose-free medium in an anaerobic chamber for 45 minutes. Cultures are then returned to the air/$CO_2$ incubator for 23 hours before analysis. Propidium iodide (PI) is used as an indicator of cell death. PI is non toxic to neurones and has been used in many studies to ascertain cell viability. In damaged neurons PI enters and binds to nucleic acids. Bound PI shows increased emission at 635 nm when excited at 540 nm. One PI fluorescence image and one white light image are taken and the proportion of cell death analysed. The area of region CA1 is defined from the white light image and superimposed over the PI image. The PI signal is thresholded and area of PI damage expressed as a percentage of the CA1 area. Correlation between PI fluorescence and histologically confirmed cell death has been validated previously by Niss1-staining using cresyl fast violet (Newell et al., *J. Neurosci.*, 1995, 15, 7702-7711).

The anti-cancer properties of compounds of the invention may be determined by the following in vitro assays:

Methylene Blue Growth Inhibition Assay (Assay 2)

Normal human foreskin fibroblasts (HFF), human melanoma (A375P, SKMEL2, SKMEL3) colon carcinoma (Colo 205) were cultured in the following growth media: A375P, Colo 205, Roswell Park Memorial Institute (RPMI) 1640 (Life Technologies 22400-089) containing 10% fetal bovine serum (FBS); HFF, Dulbecco's modified Eagle Medium (DMEM) (Life Technologies 12320-032) containing 10% FBS; SKMEL2 and SKMEL3, Minimum Essential Medium (MEM, Life Technologies 11095-080) containing 1× non-essential amino acids (Life Technologies 11140-050) and 10% FBS. Cells were harvested using 0.25% trypsin/1 mM, EDTA, counted using a haemocytometer, and plated in 10.0 microliters of the appropriate media, at the following densities, in a 96-well tissue culture plate (Falcon 3075): BFF and A375P, 5,000 cells/well; all other cell lines, 10,000 cells/well. The next day, compounds were diluted in RPMI containing 100 micrograms/ml gentamicin, at twice the final required concentration, from 10 mM stock solutions in dimethyl sulphoxide (DMSO). One hundred microliters per well of these dilutions were added to the 100 microliters of media currently on the cell plates. RPMI containing 0.6% DMSO was added to control wells. Compounds diluted in. The final concentration of DMSO in all wells was 0.3%. Cells were incubated at 37° C., 5% $CO_2$ for 3 days. Medium was removed by aspiration. Cell biomass was estimated by staining cells with 90 μl per well methylene blue (Sigma. M9140, 0.5% in 50:50 ethanol:water) and incubation at room temperature for at least 30 minutes. Stain was removed, the plates rinsed by immersion in deionized water and airdied. To release stain from the cells 100 μl of solubilization solution was added (1% N-lauroyl sarcosine, sodium salt, Sigma L5125, in phosphate-buffered saline solution (PBS)), and plates were incubated at room temperature for 30 minutes. Optical density at 620 nM was measured on a microplate reader. Percent inhibition of cell growth was calculated relative to vehicle treated control wells. Concentration of compound that inhibits 50% of cell growth ($IC_{50}$) was interpolated using nonlinear regression (Levenberg-Marquardt) and the equation, $y=V_{max}*(1-(x/(K+x)))+Y2$, where "K" was equal to the $IC_{50}$.

XTT 72 hr Growth Inhibition Protocol for Mammalian Cultured Cells (Assay 3)

Human diploid foreskin fibroblasts (HFF) or human colon carcinoma (Colo 201) cells were grown in Dulbecco's modified Eagle's medium (DMEM) (Invitrogen/Life Technologies) containing 10% fetal bovine serum (FBS) and the antibiotics penicillin (100 Units/ml) and streotomycin (100 micrograms/ml) (Invitrogen/Life Technologies). Growth was at 37° C. in humidified 5% CO2 incubators in 75 cm² plastic flasks. Cells were harvested using 0.25% trypsin/1 mM ethylenediaminetetraacetic acid (EDTA), resuspended in growth medium, and counted using a hemocytometer. Flat-bottomed 96-well plates were seeded with $2×10^3$ cells/well in a volume of 200 ul from trypsinized exponentially growing cultures. To "blank" wells, growth medium was added with no additions. Cells were incubated overnight to permit attachment.

Next day, medium from wells that contained cells was replaced with 180 microliters of fresh medium. Appropriate dilutions of test compounds were added to the wells from stock soloutions of compound dissolved in dimethyl sulfoxide (DMSO); final DMSO concentration in all wells was 0.2%. Cells plus compound were incubated for an additional 72 hr at 37° C. under normal growth conditions. Cells were then assayed for viability using standard XTT/PMS*. Fifty microliters of XTT/PMS solution was added to each well and plates were incubated for 90 minutes at 37° C. Absorbance at 450 nM was then determined using a 96-well UV plate reader (Molecular Devices). Under these conditions, absorbance of untreated control cells at 450 nm was at least 1.0 optical density unit/ml. Percent viability of cells in each well was calculated from these data (having been corrected for background absorbance). It was equal to 100×(A450 test well/A450 untreated control well), the A450s being averages of triplicate determinations. IC50 was that concentration of compound that reduced cell viability to 50% of control (untreated) viability, as determined from plots of concentration vs percent viability.

Preparation of XTT/PMS solution (immediately before assay).

For each 96-well plate, 8 mg XTT (2,3-bis[2-Methoxy-4-nitro-5-sulfophenyl]-2H-tetrazolium-5-carboxanilide) (Sigma Chemical Co.) per plate was dissolved in 100 ul DMSO. 3.9 ml $H_2O$ was added to dissolve XTT and 20 ul of PMS (phenazine methosulfate, Sigma Chemical Co.) stock solution (30 mg/ml) was added from frozen aliquoted stock solution (10 mg of PMS in 3.3 ml phosphate buffered saline (vitrogen/Life Technologies). (These stocks are routinely frozen at −20° C. until use).

Normal human foreskin fibroblasts (BFF) are the control normal cell line that should not be inhibited or at least much less sensitive.

|  |  | Cell Line Pathology | HFF normal | Colo201 Colorectal cancer | Colo205 Colorectal cancer | A375P melanoma | SKMEL3 melanoma | SKMEL2 melanoma |
|---|---|---|---|---|---|---|---|---|
|  |  | B-Raf Status | wt | ND | V599E | V599E | V599E | wt |
| B-Raf, nM Kd | Ras Status | wt | ND | wt | wt | wt | [Q61R]N-Ras |

-continued

| | Cell Line Pathology | HFF normal | Colo201 Colorectal cancer | Colo205 Colorectal cancer | A375P melanoma | SKMEL3 melanoma | SKMEL2 melanoma |
|---|---|---|---|---|---|---|---|
| Example No | Assay 1 | | Assay 2 | Assay 3 | Assay 2 | Assay 2 | Assay 2 | Assay 2 |
| 20 | 0.4 | | >30* | 0.8^Δ | 0.32^Δ | 0.31^Δ | 0.46^Δ | 1.9^Δ |

*indicates IC50 >3 μM
^Δindicates IC 50 0.3-3 μM
†indicates IC50 <0.3 μM
A375, Colo205 and SKMEL are reported as wild type (wt) for Ras status in the literature.
V599E indicates that the cell lines have activating BRaf mutation (V599E)
ND represents not determined Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of composition, process, or use claims and may include by way of example and without limitation the following claims.

The invention claimed is:

1. A compound of formula (I):

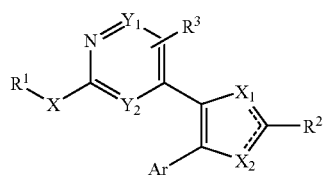

wherein:

X is O, $CH_2$, CO, S or NH, or the moiety X—$R^1$ is hydrogen;

$Y_1$ and $Y_2$ independently represent CH or N;

$R^1$ is hydrogen, $C_{1-6}$alkyl, $C_{3-7}$cycloalkyl, aryl, aryl$C_{1-6}$alkyl-, heterocyclyl, heterocyclyl$C_{1-6}$alkyl-, heteroaryl, or heteroaryl$C_{1-6}$alkyl-, any of which, except hydrogen, may be optionally substituted;

$R^2$ is $CONR^6R^7$;

$R^6$ and $R^7$ independently represent hydrogen, $C_{1-6}$alkyl, $C_{3-7}$cycloalkyl, aryl, aryl$C_{1-6}$alkyl, heteroaryl, heteroaryl$C_{1-6}$alkyl, heterocyclyl, or heterocyclyl$C_{1-6}$alkyl, any of which except for hydrogen may be optionally substituted, or $R^6$ and $R^7$ together with the nitrogen atom to which they are attached form a 3- to 12-membered monocyclic or bicyclic ring optionally including up to three heteroatoms selected from O, N or S wherein said ring may be optionally substituted;

Ar is a group of the formula a) or b):

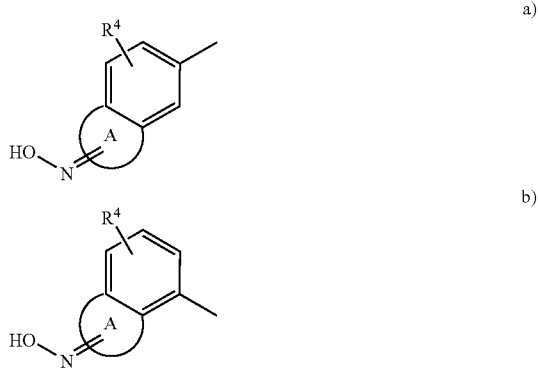

wherein A represents a fused 5- to 7-membered ring optionally containing up to two heteroatoms selected from O, S and $NR^5$, wherein $R^5$ is hydrogen or $C_{1-6}$alkyl, which ring is optionally substituted by up to 2 substituents selected from halogen, $C_{1-6}$alkyl, hydroxy, $C_{1-6}$alkoxy or keto;

$R^3$ and $R^4$ are independently selected from hydrogen, halogen, $C_{1-6}$alkyl, aryl, aryl$C_{1-6}$alkyl, $C_{1-6}$alkoxy, $C_{1-6}$alkoxy$C_{1-6}$alkyl, halo$C_{1-6}$alkyl, aryl$C_{1-6}$alkoxy, hydroxy, nitro, cyano, azido, amino, mono- and di-N-$C_{1-6}$alkylamino, acylamino, arylcarbonylamino, acyloxy, carboxy, carboxy salts, carboxy esters, carbamoyl, mono- and di-N-$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkyl sulphinyl or $C_{1-6}$alkylsulphonyl; and one of $X_1$ and $X_2$ is selected from O, S or $NR^{11}$ and the other is CH, wherein $R^{11}$ is hydrogen, $C_{1-6}$alkyl, aryl or aryl$C_{1-6}$alkyl;

or a pharmaceutically acceptable salt thereof.

2. The compound according to claim 1, wherein X—$R^1$ is hydrogen.

3. The compound according to claim 1, wherein A represents a fused 5 membered ring optionally containing up to two heteroatoms selected from O, S and $NR^5$, wherein $R^5$ is hydrogen or $C_{1-6}$alkyl, which ring is optionally substituted by up to 2 substituents selected from halogen, $C_{1-6}$alkyl, hydroxy, $C_{1-6}$alkoxy or keto.

4. The compound according to claim 1, wherein $R^6$ and $R^7$ are independently selected from hydrogen, $C_{1-6}$alkyl, aryl, heterocyclic and heterocyclic$C_{1-6}$alkyl, wherein any of the groups except hydrogen may be optionally substituted or $R^6$ and $R^7$ together with the nitrogen atom to which they are attached form a 3- to 7-membered monocyclic optionally including up to three heteroatoms selected from O, N or S wherein said ring may be optionally substituted.

5. A compound, wherein the compound is:
5-[5-(1-Morpholin-4-yl-methanoyl)-2-pyridin-4-yl-furan-3-yl]-indan-1-one oxime;
5-[5-(1-Piperidin-1-yl-methanoyl)-2-pyridin-4-yl-furan-3-yl]-indan-1-one oxime;
4-(1-Hydroxyimino-indan-5-yl)-5-pyridin-4-yl-furan-2-carboxylic acid (2-morpholin-4-yl-ethyl)-amide;
5-(5-{1-[4-(2-Methoxy-ethyl)-piperazin-1-yl]-methanoyl}-2-pyridin-4-yl-furan-3-yl)-indan-1-one oxime;
4-(1-Hydroximino-indan-5-yl)-5-pyridin-4-yl-furan-2-carboxylic acid methyl-(1-methyl-piperidin-4-yl)-amide;
5-[5-(1-[1,4']Bipiperidinyl-1'-yl-methanoyl)-2-pyridin-4-yl-furan-3-yl]-indan-1-one oxime;
5-(5-{1-[4-(4-Chloro-benzyl)-piperazin-1-yl]-methanoyl}-2-pyridin-4-yl-furan-3-yl)-indan-1-one oxime;
5-{5-[1-(4-Cyclohexyl-piperazin-1-yl)-methanoyl]-2-pyridin-4-yl-furan-3-yl}-indan-1one oxime;
5-{5-[1-(4-Methyl-piperazin-1-yl)-methanoyl]-2-pyridin-4-yl-fu ran-3-yl}-indan-1-one oxime;
5-(5-{1-[4-(2-Oxo-2-pyrrolidin-1-yl-ethyl)-piperazin-1-yl]methanoyl}-2-pyridin-4-yl-furan-3-yl)-indan-1-one oxime;
4-(1-Hydroxyimino-indan-5-yl)-5-pyridin-4-yl-furan-2-carboxylic acid 4-dimethyamino-benzylamide;
4-(1-Hydroxyimino-indan-5-yl)-5-pyridin-4-yl-furan-2-carboxylic acid (2-dimethylaminoethyl)-methylamide;
4-[({1-[4-(1-Hydroxyimino-indan-5-yl)-5-pyridin-4-yl-furan-2-yl]-methanoyl}-amino)-methyl]-piperidine-1-carboxylic acid tert-butyl ester;
4-(1-Hydroxyimino-indan-5-yl)-5-pyridin-4-yl-furan-2-carboxylic acid (2-dimethylamino-ethyl)-amide;
5-(2-Pyridin-4-yl-5-{1-[4-(2-pyrrolidin-1-yl-ethyl)-piperazin-1-yl]-methanoyl}-furan-3-yl)-indan-1-one oxime;
4-(1-Hydroxyimino-indan-5-yl)-5-pyridin-4-yl-furan-2-carboxylic acid (1-piperidin-4-yl-cyclohexylmethyl)-amide;
4-(1-Hydroxyimino-indan-5-yl)-5-pyridin-4-yl-furan-2-carboxylic acid [4-(2-dimethylamino-ethoxy)-phenyl]-amide;
4-(1-Hydroxyimino-indan-5-yl)-5-pyridin-4-yl-furan-2-carboxylic acid (2-pyrrolidin-1-yl-ethyl)-amide;
4-(1-Hydroxyimino-indan-5-yl)-5-pyridin-4-yl-furan-2-carboxylic acid [3-(4-methyl-piperazin-1-yl)-propyl]-amide;
5-{2-Pyridin-4-yl-5-[1-(4-pyrrolidin-1-yl-piperidin-1-yl]-methanoyl}-furan-3-yl}-indan-1-one oxime;
5-(5-{1-[4-(2-Dimethylamino-ethyl)-piperazin-1-yl]-methanoyl}-2-pyridin-4-yl-furan-3-yl)-indan-1-one oxime;
5-(5-{1-[4-(2-Dimethylamino-ethyl)-piperazin-1-yl]-methanoyl}-2-pyridin-4-yl-furan-3-yl)-indan-1-one oxime;
4-(1-Hydroxyimino-indan-5-yl)-5-pyridin-4-yl-furan-2-carboxylic acid (2-diisopropyl amino-ethyl)-amide;
4-(1-Hydroxyimino-indan-5-yl)-5-pyridin-4-yl-furan-2-carboxylic acid ((1R,5S)-8-methyl-azabicyclo[3.2.1]oct-3-yl)amide;
4-(1-Hydroximino-indan-5-yl)-5-pyridin-4-yl-furan-2-carboxylic acid ((1R,5S)-9-methyl-9-azabicyclo[3.3.1]non-3-yl)amide;
4-(1-Hydroxyimino-indan-5-yl)-5-pyridin-4-yl-furan-2-carboxylic acid methyl-piperidin-4-yl-amide;
5-[5-(1-Piperazin-1-yl-methanoyl)-2-pyridin-4-yl)-furan-3-yl]-indan-1-one oxime;
4-(1-Hydroxyimino-indan-5-yl)-5-pyridin-4-yl-furan-2-carboxylic acid methyl-piperidin-4-yl-amide;
5-(1-Hydroxyimino-indan-5-yl)-4-pyridin-4-yl-furan-2-carboxylic acid (2-dimethylamino-ethyl)-methyl-amide;
5-(1-Hydroxyimino-indan-5-yl)-4-pyridin-4-yl-furan-2-carboxylic acid methyl-(1-methyl-piperidin-4-yl)-amide;
5-[5-(1-[1,4']Bipiperidinyl-1'-yl-methanoyl)-3-pyridin-4-yl-furan-2-yl]-indan-1-one oxime;
5-(5-{1-[4-(4-Chloro-benzyl)-piperazin-1-yl]-methanoyl}-3-pyridin-4-yl-furan-2-yl)-indan-1-one oxime;
5-{5-[1-(4-Cyclohexyl-piperazin-1-yl)-methanoyl]-3-pyridin-4-yl-furan-2-yl}-indan-1-one oxime;
5-{5-[1-(4-Methyl-piperazin-1-yl)-methanoyl]-3-pyridin-4-yl-furan-2-yl}-indan-1-one oxime;
5-(1-Hydroxyimino-indan-5-yl)-4-pyridin-4-yl-furan-2-carboxylic acid (2-pyrrolidin-1-yl-ethyl)-amide;
5-(5-{1-[4-(2-Oxo-2-pyrrolidin-1-yl-ethyl)-piperazin-1-yl]-methanoyl}-3-pyridin-4-yl-furan-2-yl)-indan-1-one oxime;
5-(1-Hydroxyimino-indan-5-yl)-4-pyridin-4-yl-furan-2-carboxylic acid 4-dimethylamino-benzylamide;
5-(1-Hydroxyimino-indan-5-yl)-4-pyridin-4-yl-furan-2-carboxylic acid (2-diisopropylamino-ethyl)-amide;
5-(1-Hydroxyimino-indan-5-yl)-4-pyridin-4-yl-furan-2-carboxylic acid (2-diisopropylamino-ethyl)-amide;
4-[({1-[5-(1-Hydroxyimino-indan-5-yl)-4-pyridin-4-yl-furan-2-yl]-methanoyl}-amino)-methyl]-piperidine-1-carboxylic acid tert-butyl ester;
5-(3-Pyridin-4-yl-5-{1-[4-(2-pyrrolidin-1-yl-ethyl)-piperazin-1-yl]-methanoyl}-furan-2-yl)-indan-1-one oxime;
5-(1-Hydroxyimino-indan-5-yl)-4-pyridin-4-yl-furan-2-carboxylic acid (2-5hydroxy-ethyl)-amide;
5-(1-Hydroxyimino-indan-5-yl)-4-pyridin-4-yl-furan-2-carboxylic acid (2-pyrrolidin-1-yl-ethyl)-amide;
5-(1-Hydroxyimino-indan-5-yl)-4-pyridin-4-yl-furan-2-carboxylic acid (2-dimethylamino-ethyl)-amide;
5-(1-Hydroxyimino-indan-5-yl)-4-pyridin-4-yl-furan-2-carboxylic acid [3-(4-methyl-piperazin-1-yl)-propyl]-amide;
5-(1-Hydroxyimino-indan-5-yl)-4-pyridin-4-yl-furan-2-carboxylic acid (1-piperidin-1-yl-cyclohexylmethyl)-amide;
5-(1-Hydroxyimino-indan-5-yl)-4-pyridin-4-yl-furan-2-carboxylic acid [4-(2-dimethylamino-ethoxy)-phenyl]-amide;
5-(1-Hydroxyimino-indan-5-yl)-4-pyridin-4-yl-furan-2-carboxylic acid (3-dimethylamino-propyl)-amide;
5-(1-Hydroxyimino-indan-5-yl)-4-pyridin-4-yl-furan-2-carboxylic acid (2-piperidin-1-yl-ethyl)-amide;
5-(1-Hydroxyimino-indan-5-yl)-4-pyridin-4-yl-furan-2-carboxylic acid (2-amino-ethyl)-amide;
5-(1-Hydroxyimino-indan-5-yl)-4-pyridin-4-yl-furan-2-carboxylic acid piperidin-4-ylamide;
(+/−)5-(1-Hydroxyimino-indan-5-yl)-4-pyridin-4-yl-furan-2-carboxylic acid pyrrolidin-3-ylamide; and 5-(1-Hydroximino-indan-5-yl)-4-pyridin-4-yl-thiophene-2-carboxylic acid methyl-(1-methyl-piperidin-4-yl)-amide.

6. A pharmaceutical composition comprising a compound according to claim 1 or a pharmaceutically acceptable salt thereof and a pharmaceutically acceptable carrier.

7. A method for therapeutic treatment of colorectal cancer in a human, or other mammal, which comprises administering a therapeutically effective amount of a compound of claim one of formula (I) or a pharmaceutically acceptable salt thereof.

8. A method for therapeutic treatment of melanoma in a human, or other mammal, which comprises administering a therapeutically effective amount of a compound of claim one of formula (I) or a pharmaceutically acceptable salt thereof.

* * * * *